US00PP08885P

United States Patent [19]

Klemm

[11] Patent Number: Plant 8,885

[45] Date of Patent: Sep. 6, 1994

[54] GERANIUM NAMED KLEFELI

[75] Inventor: Siegfried Klemm, Stuttgart, Fed. Rep. of Germany

[73] Assignee: Klemm & Sohn, Stuttgart-Muhlhausen, Fed. Rep. of Germany

[21] Appl. No.: 173,415

[22] Filed: Dec. 23, 1993

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Tilton, Fallon, Lungmus & Chestnut

[57] ABSTRACT

A new Geranium cultivar particularly distinguished by its early flowering velvet dark red florets carried in clusters, the cultivar having medium green foliage and forming a tall bushy plant.

1 Drawing Sheet

BACKGROUND OF THE NEW PLANT

The present invention comprises a new and distinct Geranium botanically known as *Pelargonium peltatum-hybride*. The new cultivar was propagated from cuttings resulting from the cross of Velvet and Amethyst. Velvet has a dark red color that fades during the summer. Velvet has medium precocity, medium floral richness and only a few branches. Amethyst has double lavender-violet flowers, late to medium precocity, medium floral richness, and bushy but not long branches carrying leaves that suffer from Oedema. Both Velvet and Amethyst are commercially available but neither have ever been patented. In addition, neither Velvet or Amethyst are known by any other commercial names.

As a result of this cross the present cultivar was created in 1988 in Stuttgart, Germany and has been repeatedly asexually reproduced by cuttings in Stuttgart, Germany and Teneriffe, Italy over a five year period. The present cultivar has been found to retain its distinctive characteristics through successive propagations; and this novelty appears to be firmly fixed.

The new cultivar is distinguished from other dark red varieties by its precocity, floral richness and bushy growth. It most closely resembles a plant named Mexican Beauty. Mexican Beauty has red florets (RHS 46-A), however the leaves are not zonated. Mexican Beauty starts flowering much later in April and it is less vigorous and less bushy than the present cultivar. Klefeli does not change flower or leaf shape even in very hot weather and is a very good cutting producer.

DESCRIPTION OF THE DRAWING

This new Geranium plant is illustrated by the accompanying photographic drawing which shows blooms, buds, and foliage of the plant in full color, the color shown being as true as can be reasonably obtained by conventional photographic procedures.

DESCRIPTION OF THE NEW CULTIVAR

The following detailed descriptions set forth the distinctive characteristics of this new Geranium. The data which defines these characteristics was collected from asexual reproductions carried out in Stuttgart, Germany. The plant history was taken on 10 week old plants, blossomed under natural light in a greenhouse. Color readings were taken in the greenhouse under ambient light. Color references are primarily to The R.H.S. Colour Chart of The Royal Horticultural Society of London.

THE PLANT

Classification:
- *Botanical.*—*Pelargonium peltatum-hybride.*
- *Commercial.*—Ivy Geranium.

Parentage:
- *Seed parent.*—Velvet.
- *Pollen parent.*—*Dresdner dunkle* Amethyst.

Form: Compact bush with long dropping vines.

Height of plant: 160–170 mm after 10 weeks.

Stem length: 170–220 mm in June and 290–320 mm in September.

Branching character:
- *Number of stems per stalk.*—7 (in July).
- *Number of stalks per plant.*—9 (in July).
- *Internode length.*—About 5–12 mm depending on the light where the plant is propagated and the method of propagation.
- *Growth rate.*—If propagated in January, the blooms can be sold in April without pinching.
- *Strength.*—It grows early and powerfully with many branches.

Foliage:
- *Quantity.*—Abundant.
- *Size.*—Between 50×80 mm and 70×60 mm.
- *Shape.*—Ivy-shaped.
- *Margin.*—No creations.
- *Texture.*—Leathery.
- *Ribs and veins.*—None.
- *Color.*—Upper side: Medium green — RHS 137-A with a dark center — RHS 147-A.
- *Under side.*—Green — RHS 147-B.
- *Leaf petiole.*—50–60 mm.

THE BUD

Size:
- *Diameter.*—About 6 mm.
- *Length.*—About 12 mm.

Shape: Elliptic.

Form: Pointed.

Rate of opening: Medium.

Color: Of the petals when sepals first divide, white and pink; when petals begin to unfurl, dark red.

Sepals:
- *Number.*—5.
- *Shape.*—Very Long and Pointed.

*Color.*—Inside — light green — RHS 146-C. Outside — light green — RHS 146-B.

*Form.*—Standing up.

Petiole of floret:

*Length.*—About 23 mm.

*Strength.*—Erectly arranged hemispherically around the end of the cluster stalk.

*Color.*—Green — RHS 146-A.

THE FLOWER

Blooming habit: Klefeli blooms in April and then continuously and very profusely until a frost. The number of umbels on 3 plants varied from 190 to 225 per plant in outside trials.

Size of floret: Approximately 47–48 mm×8 mm.

Born: In a cluster about 80–90 mm in diameter.

Shape: When the bloom first opens the blooms are flat. The blooms do not change in shape.

Petals:

Number.—About 16 per floret.

*Arrangement.*—Imbricated.

*Form.*—Not very broad.

*Color.*—Outer petal: body and base are cardinal red-RHS 53-B. Inside petal: body and base are cardinal red-RHS 53-B. Reverse side: tyrian purple RHS 57-A.

*Texture.*—Soft.

*Appearance.*—Satiny.

*How long do petals remain on stem.*—About five days depending on the weather.

Petaloids: None.

Cluster stem:

*Length.*—90–110 mm.

*Color.*—Green — RHS 146-A.

*Characteristics.*—Upright and horizontal.

Persistence: Matured florets or clusters should be picked off.

Disease resistance: The present cultivar has a certain resistance against Botyrtis.

Weather resistance: The present cultivar is not unusually affected by wet or hot weather.

Lasting quality:

*On the plant.*—About 13–17 days.

*As a cut flower.*—About 6 days.

Fragrance: No perceptible fragrance.

REPRODUCTIVE ORGANS

Stamens:

*Anthers.*—4–6 positioned around the ovaries with 2.1 mm length.

*Filaments.*—8–9 mm in length and white and red.

Pollen: Orange in color.

Pistils:

*Number.*—One.

*Length.*—Approximately 7 mm.

*Stigmas.*—Red in color.

Ovaries: Green in color.

Seed: Not fertile.

I claim:

1. A new and distinct Geranium cultivar substantially as herein shown and described, particularly distinguished by its early flowering velvet dark red florets carried in clusters, said cultivar having medium green foliage and which forms a tall bushy plant.

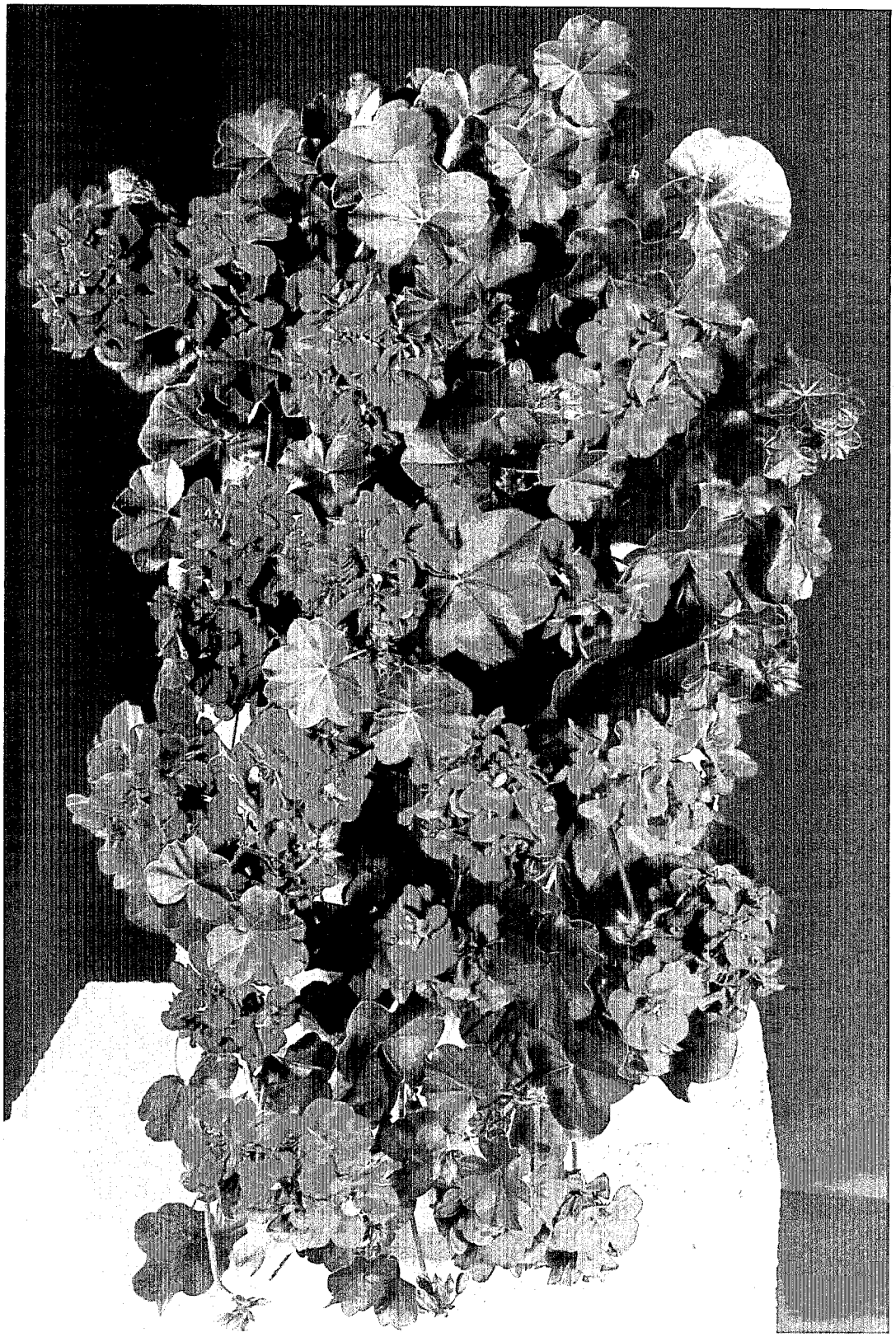

* * * * *